United States Patent
Horrobin et al.

(10) Patent No.: US 6,369,041 B2
(45) Date of Patent: *Apr. 9, 2002

(54) ORAL COMBINATIONS OF HYDROXOCOBALAMIN AND FOLIC ACID

(75) Inventors: David Frederick Horrobin, Stirling (GB); Christina Gouaille, Helsingborg (SE)

(73) Assignee: Kilgowan Limited, Douglas Isle of Man (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/534,417

(22) Filed: Mar. 23, 2000

(30) Foreign Application Priority Data

Mar. 23, 1999 (GB) ............................................... 9906740

(51) Int. Cl.$^7$ ............................................... A61K 31/70
(52) U.S. Cl. ....................................................... 514/52
(58) Field of Search ........................................... 514/52

(56) References Cited

U.S. PATENT DOCUMENTS

| 5,545,670 A | * | 8/1996 | Bissbort et al. | 514/562 |
| 5,795,873 A | * | 8/1998 | Allen | 514/52 |
| 6,121,249 A | * | 9/2000 | Weissman et al. | 514/52 |
| 6,129,918 A | * | 9/2000 | Amagase | 424/195.1 |

FOREIGN PATENT DOCUMENTS

| DE | 4326698 A1 | 3/1995 | .......... A61K/31/68 |
| EP | 558 960 A1 | 9/1993 | |
| EP | 0 595 005 A1 | 5/1994 | |
| EP | 0 951 842 A3 | 10/1999 | |
| EP | 0 951 842 A2 | 10/1999 | |
| GB | 821398 | 10/1959 | |

OTHER PUBLICATIONS

The natural history of vascular disease in homocystinuria and the effects of treatment; D.E.L. Wilcken et al., Journal of Inherited Metabolic Disease, vol. 20, No. 2, Jun. 1997, 295–300.
Vitamin Supplementation Reduces Blood Homocysteine Levels; Martin den Heijer, et al., Arteriosclerosis, Thrombosis, and Vascular Biology, vol. 18, No. 3 (1998) 356–361.
Improvement in Bronchial Squamous Metaplasia in Smokers Treated with Folate and Vitamin $B_{12}$,; D.C. Heimburger et al., JAMA, vol. 259, No. 10 (1988) 1525–1530.
Oral Treatment of Pernicious Anemia With High Doses of Vitamin $B_{12}$ Without Intrinsic Factor; Hans Berlin, et al.; Acta med. scand. vol. 184, pp. 247–258, 1968.
Chem. Abs. 128:223120 & Arterioscler., Tromb., Vasc. Biol., 18(3), 356–61, (1998).
M.den Heijer et al,"Vitamin supplementation reduces blood homocysteine levels: a controlled trial in patients with venous thrombosis and healthy volunteers".
Administration of folic acid, hydroxycobalamin and pyridoxine as a multivitamin supplement to reduce homocysteine levels.

* cited by examiner

Primary Examiner—James H. Reamer
(74) Attorney, Agent, or Firm—Darby & Darby

(57) ABSTRACT

A variety of conditions is known wherein vitamin $B_{12}$ is deficient, or wherein the administration of vitamin $B_{12}$ is beneficial.

Classically, once detected and if appropriate, these have been treated by the parenteral administration of vitamin $B_{12}$ as oral administration is believed to be ineffective. Available oral preparations of vitamin $B_{12}$ all contain cyanocobalamin which is less desirable than hydroxocobalamin.

In accordance with the invention, effective oral formulations are provided which include, in addition to the hydroxocobalamin, folic acid or other folate precursor. The formulation for oral administration should be such as to provide, for a given daily dose, 0.5 to 59 mg hydroxocobalamin and 0.5 to 50 mg folic acid.

15 Claims, No Drawings

ORAL COMBINATIONS OF HYDROXOCOBALAMIN AND FOLIC ACID

FIELD OF THE INVENTION

This invention relates to the field of treating vitamin deficiency conditions and to preparations for use in such treatment.

BACKGROUND OF THE INVENTION

Vitamin $B_{12}$ is a cobalt-containing vitamin which is involved in a number of biochemical reactions. The two most important are the conversion of homocysteine to methionine and the conversion of methylmalonyl-coenzyme A to succinyl-coenzyme A. Homocysteine is potentially harmful to many body tissues, including the vascular system and the nervous system, if it is present in excess. Methionine is required for the formation of S-adenosyl-methionine which is used as a methyl donor in many different essential reactions including the regulation of DNA and RNA function and the synthesis of phospholipids, neurotransmitters and complex carbohydrates. The formation of succinyl-coenzyme A is required for the normal metabolism of fats and carbohydrates. It is thus apparent that an inadequate supply of vitamin $B_{12}$ will lead to many different abnormalities in the body. The best known are the haematological abnormality of megaloblastic anaemia, and neurological damage which can lead to fatigue and to a range of neurological and psychiatric symptoms which are caused by loss of neuronal function proceeding to neurodegeneration.

Vitamin $B_{12}$ has a particularly close interaction with folic acid. The conversion of homocysteine to methionine is achieved by the enzyme methionine synthetase where methyl-cobalamin plays an essential role. A required co-factor for this enzyme is folic acid in the form of 5-methyltetrahydrofolate: in the course of the reaction a methyl group is transferred from 5-methyltetrahydrofolate to homocysteine, so producing tetrahydrofolate and methionine. As a result of this reaction deficiencies of folic acid and of vitamin $B_{12}$ interact. This interaction is important both in the lowering of homocysteine and in the generation of S-adenosyl-methionine for methylation reactions.

Methylation is increasingly being recognised as a reaction of central importance in many different reactions in all the tissues of the body, but particularly the brain, the liver and rapidly dividing tissues like the bone marrow, the gastrointestinal tract, the skin and the reproductive system. The methyl donor which plays the key role in over thirty reactions is S-adenosyl-methionine (SAM) (T Bottiglieri et al, Drugs 1994; 48; 137–152. P K Chiang et al, FASEB J 1996; 10; 471–480. T Bottiglieri, Exp Opin Invest Drugs 1997; 6; 417–426. C S Lieber, J Hepatology 1999; 30; 1155–9). Methylation of the nucleic acids, DNA and RNA, plays a central role in the regulation of gene function and expression. Methylation regulates the functions of many enzymes, including enzymes involved in the synthesis of the neurotransmitters noradrenaline, dopamine and serotonin. Methylation modulates the behaviour of many receptors, including those for noradrenaline, adrenaline, acetyl choline, gamma-amino-butyric acid and many other substances. Methylation is important in the synthesis of key membrane phospholipids and in the regulation of the properties of all the external and internal phospholipid-containing membranes of cells. Methylation is required for the normal synthesis of the polyamines, spermine and spermidine, which are important signalling molecules in many cells. Methylation is important in the synthesis of complex carbohydrates which modify many cell-cell interactions. Since vitamin $B_{12}$ and folic acid are absolutely required for the normal synthesis of SAM, it is clear that it is of central importance that they should always be available in all tissues in adequate amounts. Recently, SAM and stable derivatives thereof have themselves been developed as drugs, particularly for nervous system and liver diseases (Bottiglieri, 1997, Lieber, 199).

As well as being converted to methionine, homocysteine can also be converted to cystathionine and then to cysteine in two successive reactions, both of which require vitamin $B_6$ as a co-factor. Excessive accumulation of homocysteine can thus be partially dealt with by its metabolism along this pathway. However, this cannot occur if there is inadequate availability of vitamin $B_6$. Vitamin $B_6$ may, therefore, be of value in removing homocysteine, but not in generating SAM since it takes homocysteine out of the cycle.

There are four main forms of vitamin $B_{12}$, cyanocobalamin, hydroxocobalamin, methylcobalamin and adenosylcobalamin. Methylcobalamin and adenosylcobalamin are unstable and very easily damaged by light. They are therefore unsuitable for use in dietary supplements or pharmaceuticals and are not necessary since they can be formed from cyanocobalamin or hydroxocobalamin within the body. The main form of vitamin $B_{12}$ found in food is hydroxocobalamin (J Farquharson and J F Adams, British Journal of Nutrition 1976; 36:127–136). The main form used therapeutically and in nutritional supplements is cyanocobalamin, chosen because it is the most stable form and therefore easiest to synthesise and formulate. All oral nutritional and pharmaceutical preparations of vitamin $B_{12}$ which are commonly available use cyanocobalamin.

In normal individuals vitamin $B_{12}$ is absorbed from the gastro-intestinal tract with the aid of a specific binding protein, known as intrinsic factor (IF) which is produced by the stomach. The normal daily requirement for vitamin $B_{12}$ is in the region of 0.1 to 2.0 microg/day according to various expert committees. There is normally an extensive enterohepatic recovery of vitamin $B_{12}$. This recovery is impaired if IF is lacking, if the distal ileum is damaged, e.g. by radiation or disease, or has been removed by surgery. The daily loss of vitamin $B_{12}$ can be then considerably increased, at the same time as the food-bound vitamin $B_{12}$ cannot be absorbed. A lack of IF thus produces a deficit of vitamin $B_{12}$ within the body even though there are apparently adequate amounts in the food. The deficiency, known as pernicious anaemia, is treated by injections of vitamin $B_{12}$ as cyanocobalamin or hydroxocobalamin as it is generally believed that oral administration of vitamin $B_{12}$ will be ineffective.

However, it is not well known that it is possible to treat vitamin $B_{12}$ deficiency by oral administration of mg-doses even in the absence of IF, or when absorption is disturbed by other causes. This is because there is also a passive diffusion of the vitamin through the intestinal wall into the body without any need for IF. The passive absorption is dose-dependent and amounts to about 1–2% of doses of 1 mg or more. Two studies using cyanocobalamin have shown that oral doses of 1–2 mg/day are fully adequate to provide vitamin $B_{12}$ even in patients with pernicious anaemia (H Berlin et al, Acta Medica Scandinavica 1968; 184:247–258: A M Kuzminski et al, Blood 1998; 92:1191–8). Long-term oral treatment with 1 mg cyanocarbalamin per day has been calculated to restore the body stores of vitamin $B_{12}$ to the same extent as 1 mg hydroxocobalamin given by injection each third month (Berlin R et al, Acta Medica Scan. 1978; 204:81–4). However it is not well known by doctors that a vitamin $B_{12}$ deficiency can be treated orally: in a survey of 245 internal medicine specialists in Minnesota none had used oral vitamin $B_{12}$ to treated pernicious anaemia and only 1% had used oral vitamin $B_{12}$ to treat a dietary deficiency: injection of cyanocobalamin was the treatment used by those doctors (F A Lederle, JAMA 1991; 265:94–95).

Recent studies have demonstrated that vitamin $B_{12}$ deficiency states are much commoner in the general population, especially in the older population, in smokers, and in those at risk of cardiovascular disease than had previously been thought. One marker of this is an elevated level of homocysteine in plasma. For example, 44 apparently healthy men had elevated levels of homocysteine coupled with highly significantly subnormal blood levels of vitamin $B_{12}$ (J B Ubbink et al, American Journal of Clinical Nutrition 1993; 57:47–53). A high proportion of older outpatients attending a clinic had deficiencies of vitamin $B_{12}$ (L C Pennypacker et al, Journal of the American Geriatric Society 1992; 40:1197–1204). In a Massachusetts population 40.5% of older individuals and 17.9% of younger people were found to have low or low normal serum vitamin $B_{12}$ (J Lindenbaum et al, American Journal of Clinical Nutrition 1994; 60:2–11). In Europe 63% of healthy elderly people were found to have an elevated level of homocysteine or methylmalonic acid, or other markers of vitamin $B_{12}$ deficiency (E Joosten et al, American Journal of Clinical Nutrition 1993; 58:468–76). In healthy older Dutch people, 23.8% were found to be vitamin $B_{12}$ deficient (DZB van Asselt el al, American Journal of Clinical Nutrition 1998; 68:328–334). In many of the individuals reported in these studies there were also deficiencies of folate and sometimes of vitamin $B_6$ which exaggerated the problems associated with vitamin $B_{12}$ deficiency.

Most of the people with these deficiencies apparently have adequate vitamin $B_{12}$ levels in the diet. Their problems must therefore relate to inadequate levels of IF or to some other metabolic problem. If there are deficits of IF, standard medical treatment is to give injections of vitamin as hydroxocobalamin or cyanocobalamin and not oral treatment. However, to give regular injections to the very large numbers of apparently healthy people affected by vitamin $B_{12}$ deficiency is clearly not a practical proposition. Oral vitamin $B_{12}$ is usually given only when there is a dietary deficiency. Then the form of the vitamin which is given is always cyanocobalamin: no oral preparations of hydroxocobalamin are available.

Surprisingly, we have noted that cyanocobalamin may be less than optimum and may even be toxic in individuals with vitamin $B_{12}$ deficiency. One reason is that there appear to be adverse interactions between vitamin $B_{12}$ deficiency and the presence of cyanide. Cyanide is relatively common at low levels in the environment, being present in smoke, particularly tobacco smoke, and in certain foods. It may also be generated in small amounts in the course of normal metabolism since the body contains effective mechanism for cyanide detoxification. There is evidence that the consequences of vitamin $B_{12}$ deficiency for the nervous system are much more serious in the presence of situations where cyanide may be generated or not detoxified (A G Freeman, Journal of the Royal Society of Medicine 1988; 81:103–106: A G Freeman, Journal of the Royal Society of Medicine 1992; 85:686–7). Whereas cyanocobalamin will not alleviate any cyanide excess and may even make the situation worse because of its cyanide content, hydroxocobalamin not only corrects a vitamin $B_{12}$ deficiency but actually acts as an antidote to cyanide poisoning by binding cyanide (J C Forsyth et al, Clinical Toxicology 1993; 31:277–294). On the basis of these observations, therefore, Freeman has argued that cyanocobalamin should actually be withdrawn and replaced by hydroxocobalamin. However, Freeman has also argued that only hydroxocobalamin given by injection should be used, stating "I strong oppose any treatment for pernicious anaemia other than parenteral hydroxocobalamin" (A G Freeman 1999; Lancet 353:410–411).

General Description of the Invention

In view of the widespread occurrence of vitamin $B_{12}$ deficiency states in the general population, in view of the fact that most of these deficiency states are not due to lack of vitamin $B_{12}$ in food, and in view of the potential toxicity or lack of efficacy of high doses of cyanocobalamin, we propose the formulation of high doses of hydroxocobalamin for oral administration. Furthermore in view of the very common co-occurrence of folate deficiency in these same populations and in view of the fact that folate and vitamin $B_{12}$ are so closely linked metabolically we propose that the hydroxocobalamin should always be formulated with folic acid or a related compound with folate bioactivity such as methyltetrahydrofolate. Such formulations will be particularly valuable in generating SAM for methylation reactions.

In order to ensure adequate absorption of vitamin $B_{12}$, even in the absence of intrinsic factor, we propose that the formulation should provide a minimum dose of 0.5 mg hydroxocobalamin per day, should sometimes include more than 5 mg/day and should provide a maximum dose of 50 mg per day, preferably within the range of 1 mg per day to 10 mg/day. The hydroxocobalamin should be formulated with folic acid or a related bioactive derivative also providing a minimum of 0.5 mg folate per day and a maximum of 50 mg/day.

There is an extensive literature relating to the uses of folic acid and of vitamin $B_{12}$, particularly in relation to the lowering of homocysteine levels. There is less literature relating to their uses in situations where enhancement of methylation is important. Almost all of the literature deals with the use of folic acid combined with cyanocobalamin as the source of the vitamin $B_{12}$. Occasional authors mention hydroxocobalamin in passing as a possible alternative source, but none emphasises or even discusses the advantages of using hydroxocobalamin in view of the potential toxicity of cyanocobalamin.

Three citations are of particular importance in the context of the combined use of high or relatively high doses of vitamin $B_{12}$ and folic acid. A patent EP-A-0558960 in the name of Wörwag discloses primarily the use of thiamin, in association with other nutrients, in medicaments for patients whose are abusing alcohol. This specification describes folic acid and vitamin $B_{12}$ as additional ingredients to thiamine in such a medicament. Any form of vitamin $B_{12}$ is described as being acceptable in the formulation, with no discussion of the possible toxicity of cyanocobalamin or of the advantages of hydroxocobalamin. Thiamine is always an essential component and the specification does not disclose the value of formulation of hydroxocobalamin and folic acid.

EP-A-0595005 Vesta discloses the combination of three nutrients, folic acid, vitamin $B_{12}$ and vitamin $B_6$, specifically for the treatment of elevated homocysteine levels. Vitamin B6 is absolutely required in this formulation. The source of vitamin B12 is stated as being cyanocobalamin or hydroxocobalamin. There is no suggestion that hydroxocobalamin is the preferred form, or that cyanocobalamin may potentially be toxic. All of the examples of oral products specifically refer to cyanocobalamin and not to hydroxocobalamin.

A paper by M den Heijer et al (Arterioscler Thromb Vasc Biol 1998; 18; 356–61) discusses the administration of a formulation for lowering homocysteine levels comprising 0.4 mg of hydroxocobalamin, either alone or with 0.5 mg/day or 5 mg/day of folic acid. The authors found that hydroxocobalamin contributed little to the lowering of homocysteine levels with the main effect being due to folic acid. The dose of hydroxocobalamin in this citation is lower than provided for in the present specification and is probably too low to be consistently beneficial in individuals who have any problems in the absorption or metabolism of vitamin $B_{12}$.

Thus, none of the prior art describes the specific importance of higher oral doses of hydroxocobalamin of 0.5 mg/day or above when combined with folic acid. None of the prior art discusses the specific uses of hydroxocobalamin and folic acid to promote the synthesis of SAM for methylation reactions.

As discussed above, there is increasing interest in using SAM, or derivatives of SAM, as therapeutic agents themselves for the promotion of methylation reactions. Once SAM has donated its methyl group, the molecule left is S-adenosyl-homocysteine, which is rapidly converted to homocysteine. Thus, administration of SAM has the potential to increase the formation of homocysteine substantially, particularly in patients with deficits of folic acid of vitamin $B_{12}$ who may not be able to metabolise the homocysteine normally. It will therefore be particularly appropriate to include hydroxocobalamin and folic acid in formulations of SAM or derivatives of SAM for any therapeutic purpose for which the SAM is being administered.

Other ingredients may optionally be added to the basic hydroxocobalamin/folate formulation. These may include any other essential nutrients and any drugs. Such formulations will be particularly appropriate when treatment is given to a population which seems to be at particular risk of, or particularly affected by single or combined deficiencies of vitamin $B_{12}$ or folate. Such patients include all elderly patients being treated for any disease, all patients of any age being treated for psychiatric or neurological diseases, including patients with depression, bipolar disorder, schizophrenia, multiple sclerosis, dementias, including Alzheimer's disease, panic attacks, anxiety, social phobia, and Parkinson's disease, all patients with fatigue of any origin, and all patients with or at risk of cardiovascular disease, liver diseases, gastrointestinal, reproductive or skin diseases, or any other diseases. These populations for various reasons are often at risk of nutritional deficiencies and deficiencies of vitamin $B_{12}$ or folic acid may often limit the desired therapeutic responses to drug treatment of any of the above illnesses. It is therefore within the scope of the invention to add hydroxocobalamin and folic acid to any oral formulation of any drug for the treatment of the above diseases.

SPECIFIC EXAMPLES OF THE INVENTION

EXAMPLES

1. A tablet or hard or soft gelatin capsule containing between 0.5 and 50 mg of hydroxocobalamin together with between 0.5 mg and 50 mg of folic acid.

2. A flavoured syrup containing in 5 ml between 0.5 and 50 mg of hydroxocobalamin together with between 0.5 mg and 50 mg of folic acid.

3. A sugar-flavoured powder containing between 0.5 and 50 mg of hydroxocobalamin and between 0.5 mg and 50 mg of folic acid in 5 g.

4–6. As 1–3 but containing in addition 2–100 mg of vitamin $B_6$.

7–12. Multinutrient formulations for oral use containing a range of essential nutrients, in which are included folic acid and hydroxocobalamin as specified in examples 1–6.

13. A drug for oral use in the treatment of any disease whose daily formulation includes hydroxocobalamin and folic acid as in formulation 1.

14. A drug for oral use in cardiovascular disease formulated as in 13.

15. A drug for oral use in psychiatric or neurological disease formulated as in 13.

16. A drug for oral use in the treatment of any disease in people over the age of 40 formulated as in 13.

17. S-adenosyl-methionine (SAM), or derivatives of SAM, formulated for oral administration as in 13.

We claim:

1. An orally administrable formulation containing hydroxocobalamin and folic acid or a related bioactive derivative of folic acid, the concentrations of each being such as to provide in a daily specified dosage of the formulation between 0.5 and 50 mg of hydroxocobalamin and between 0.5 and 50 mg of folic acid.

2. A formulation according to claim 1 where the concentration of hydroxocobalamin is such as to provide in the daily dosage more than 5 mg.

3. A formulation according to claim 1 which contains no other essential nutrients.

4. A formulation according to claim 2 which contains no other essential nutrients.

5. A formulation according to claim 1 which, in addition, contains vitamin $B_6$ in a concentration to provide in the daily specified dosage 0.5 mg to 200 mg of vitamin $B_6$.

6. A formulation according to claim 1 which, in addition, contains vitamin $B_6$ in a concentration to provide in the daily specified dosage more than 50 mg of vitamin $B_6$.

7. A formulation according to claim 2 which, in addition, contains vitamin $B_6$ in a concentration to provide in the daily specified dosage 0.5 mg to 200 mg of vitamin $B_6$.

8. A formulation according to claim 2 which, in addition, contains vitamin B6 in a concentration to provide in the daily specified dosage more than 50 mg of vitamin B6. vitamin B6.

9. A formulation according to claim 1 which additionally contains one or more other essential nutrients.

10. A formulation according to claim 1 which additionally contains a drug which can be used for treating, alleviating or preventing any illness.

11. A formulation according to claim 10 wherein the drug is a drug for the treatment, alleviation or prevention of cardiovascular disease.

12. A formulation according to claim 10 wherein the drug is a drug for the treatment, alleviation or prevention of any psychiatric or neurological disorder, including disorders of both the peripheral and central nervous system.

13. A formulation according to claim 10 wherein the drug is a drug for the treatment, alleviation or prevention of any disorder of the liver, gastrointestinal tract, bone marrow, skin or reproductive system.

14. A formulation according to claim 10 wherein the drug is S-adenosyl-methionine or any derivative thereof.

15. A method of treating vitamin $B_{12}$ and/or folic acid deficiency conditions, or conditions where increased intake of vitamin $B_{12}$ and/or folic acid is clinically effective even in the absence of a recognised deficiency, which comprises the oral administration of a formulation in accordance with claim 1.

* * * * *